United States Patent
Baraldi (10) Patent No.: US 8,403,874 B2
(45) Date of Patent: Mar. 26, 2013

(54) MACHINE FOR EXTRACORPOREAL BLOOD TREATMENT

(75) Inventor: Vincenzo Baraldi, Quistello (IT)

(73) Assignee: Gambro Lundia AB, Lund (SE)

( * ) Notice: Subject to any disclaimer, the term of this patent is extended or adjusted under 35 U.S.C. 154(b) by 614 days.

(21) Appl. No.: 11/996,730

(22) PCT Filed: Nov. 24, 2005

(86) PCT No.: PCT/IB2005/003536
§ 371 (c)(1),
(2), (4) Date: Jan. 24, 2008

(87) PCT Pub. No.: WO2007/012915

PCT Pub. Date: Feb. 1, 2007

(65) Prior Publication Data

US 2008/0221496 A1   Sep. 11, 2008

(30) Foreign Application Priority Data

Jul. 29, 2005   (IT) .............................. MO2005A0195

(51) Int. Cl.
*A61M 37/00* (2006.01)
(52) U.S. Cl. ....................................... 604/4.01; 604/154
(58) Field of Classification Search ........ 604/4.01–6.16, 604/28, 30–34, 51, 65–67, 151, 154, 200–206, 604/207–211, 228, 131; 600/432
See application file for complete search history.

(56) References Cited

U.S. PATENT DOCUMENTS

| | | | |
|---|---|---|---|
| 3,336,925 A | | 8/1967 | Thompson |
| 4,082,094 A | * | 4/1978 | Dailey ........................ 604/93.01 |
| 4,769,009 A | | 9/1988 | Dykstra |
| 5,545,140 A | | 8/1996 | Conero et al. |
| 5,650,071 A | * | 7/1997 | Brugger et al. ............... 210/646 |
| 5,651,775 A | * | 7/1997 | Walker et al. ................. 604/207 |
| 5,814,015 A | * | 9/1998 | Gargano et al. ................. 604/67 |
| 2002/0198496 A1 | | 12/2002 | Duchon et al. |
| 2003/0040719 A1 | * | 2/2003 | Spohn et al. .................. 604/228 |
| 2003/0120212 A1 | * | 6/2003 | Dedig et al. .................. 604/151 |
| 2004/0249276 A1 | * | 12/2004 | Nemoto et al. ............... 600/432 |
| 2005/0096593 A1 | * | 5/2005 | Pope et al. .................... 604/122 |

FOREIGN PATENT DOCUMENTS

| | | |
|---|---|---|
| EP | 1 486 219 A1 | 12/2004 |
| JP | 2003-220136 A | 8/2003 |

* cited by examiner

*Primary Examiner* — Philip R Wiest
(74) *Attorney, Agent, or Firm* — Pearne & Gordon LLP (57) ABSTRACT

In a machine for extracorporeal blood treatment, a syringe pump (4) for infusion of an anticoagulant comprises a support (5) for the syringe, a pusher (6), a sensor of the pushing force of the pusher (6), and a control unit (8) for guiding the pusher (6) in accordance with the force measured by the sensor. The support comprises a series of interchangeable gripping elements (9), each of which defines a housing for a syringe having a different diameter, the housing having a longitudinal axis which, for all of the interchangeable gripping elements in the series, is always in the same position in relation to the pusher. The invention provides a dialysis machine with a pump that is easily and rapidly adaptable for syringes over a wide range of sizes.

11 Claims, 7 Drawing Sheets

MACHINE FOR EXTRACORPOREAL BLOOD TREATMENT

BACKGROUND OF THE INVENTION

The invention relates to a machine for extracorporeal blood treatment.

Specifically, though not exclusively, the machine can be usefully applied in a machine for treatment of renal insufficiency, and/or for therapeutic replacement of plasma, and/or for hemoperfusion.

As is known, a machine for extracorporeal blood treatment is operatively associated to a circuit for extracorporeal blood treatment. Also well known is an injection system of an anticoagulant liquid into an extracorporeal circuit for reducing a risk of coagulation in the extracorporeal circuit. The injection system usually comprises a syringe pump for injection of relatively low and precise flows of anticoagulant. The syringe pump generally comprises a removable syringe, a support predisposed on the front panel of the machine for receiving and removably holding the syringe in position, a linear pusher for moving the syringe plunger, a sensor for emitting a signal indicating the push force exerted on by the pusher, and a control unit for receiving the above-mentioned signal and for guiding the linear pusher in accordance with the signal received.

One of the problems of known-type machines for extracorporeal blood treatment consists in the adaptability thereof to syringes of various sizes. The syringe supports used at present enable safe and reliable mounting of a relatively limited range of syringes. Also, when the syringe size is changed, the position of the longitudinal axis of the syringe changes with respect to the pusher; consequently it is necessary to take this change into consideration when calculating the thrust force the pusher must exert in order to obtain the desired anticoagulant flow rate. A further problem is ascertaining surely and reliably the type of syringe which is in use by the syringe pump, in order to prevent errors in the anticoagulant flow rate which might turn out to be considerably dangerous for the patient.

SUMMARY OF THE INVENTION

A main aim of the present invention is to provide a machine for extracorporeal blood treatment, which is able to overcome the above-described limitations and drawbacks.

A further aim of the invention is to realise a machine which is relatively simple and economical and which is easy and immediate to use.

An advantage of the invention is to provide a machine having a syringe pump which is easily and rapidly adaptable for syringes over a wide range of sizes.

A further advantage is that the invention provides a machine having a syringe pump which guarantees correct positioning of the longitudinal axis of the syringe whatever the size of the syringe.

A further advantage is that the invention provides a machine having a syringe pump in which the risk of an erroneous recognition of the type of syringe being used is reduced to a minimum.

These aims and advantages and more besides are all attained by the present invention, as it is characterised in one or more of the appended claims.

Further characteristics and advantages of the present invention will better emerge from the detailed description that follows, of at least one preferred embodiment of the invention, illustrated by way of non-limiting example in the accompanying figures of the drawings.

BRIEF DESCRIPTION OF THE DRAWINGS

The description will now be made with reference to the appended figures of the drawings, provided by way of non-limiting example, in which.

DETAILED DESCRIPTION

Figure 1:
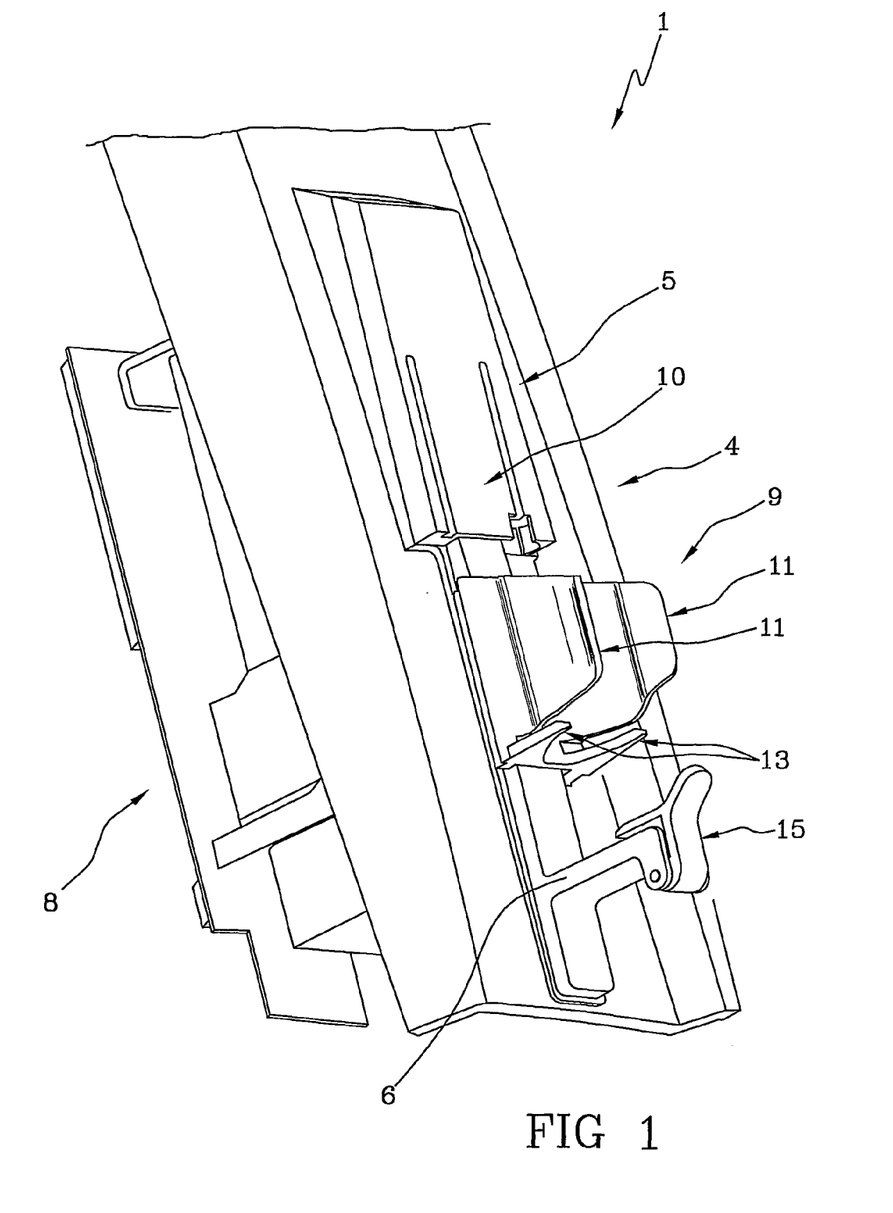
FIG. 1 is a partial perspective view of a machine for dialysis made according to the invention, in which the syringe pump support for infusion of anticoagulant is shown, during a mounting stage of the interchangeable gripping element of the support.
Figure 2:
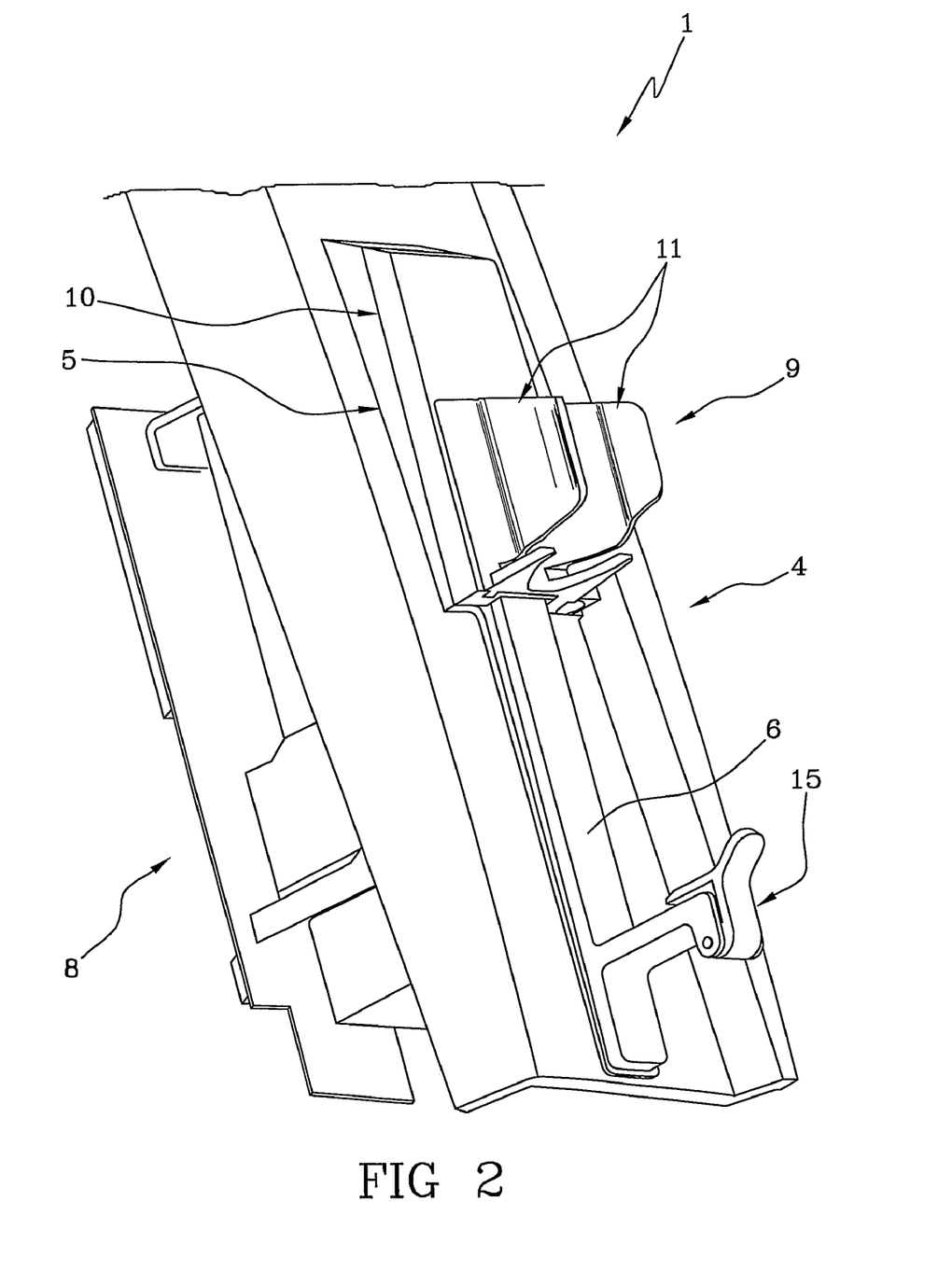
FIG. 2 is the view of FIG. 1, in which the interchangeable gripping element is mounted in the seating therefor.
Figure 3:
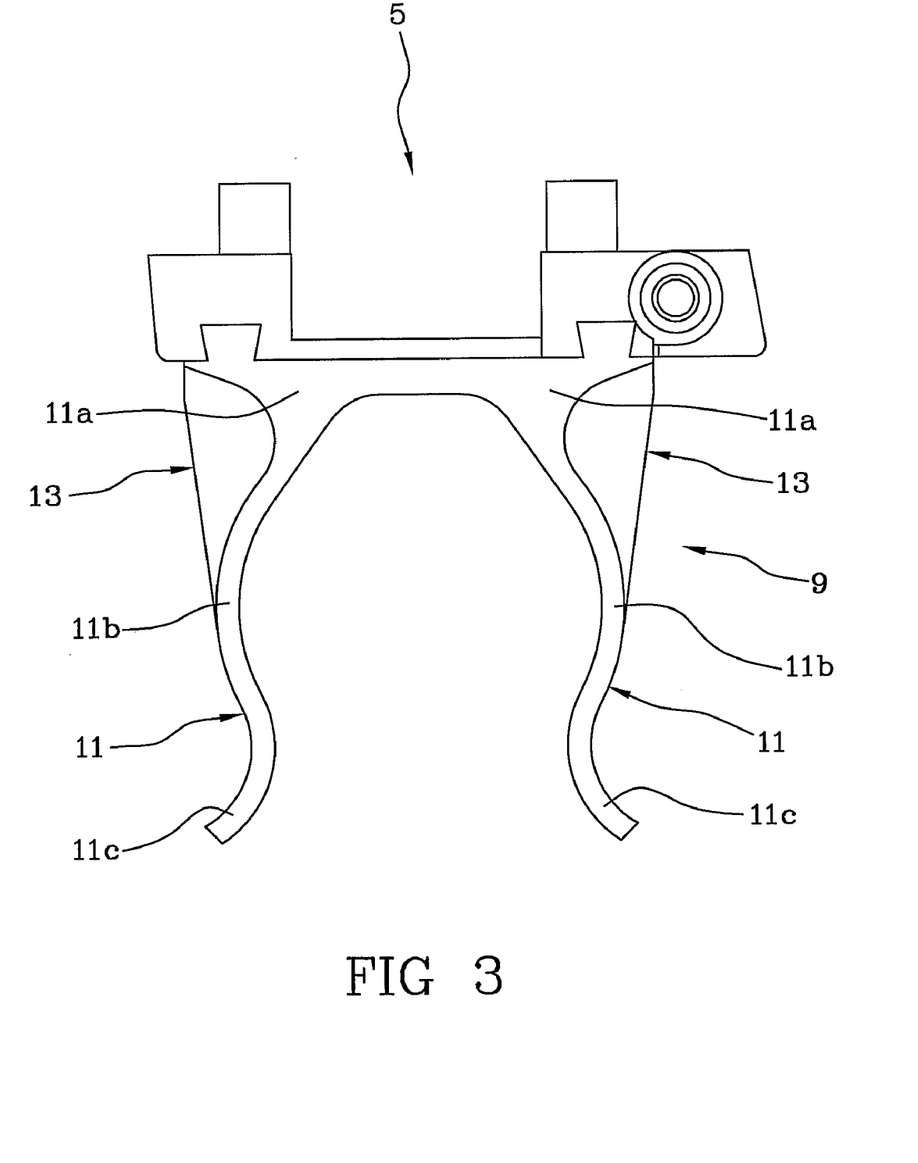
FIG. 3 is a view from above of the support of FIG. 2.
Figure 4:
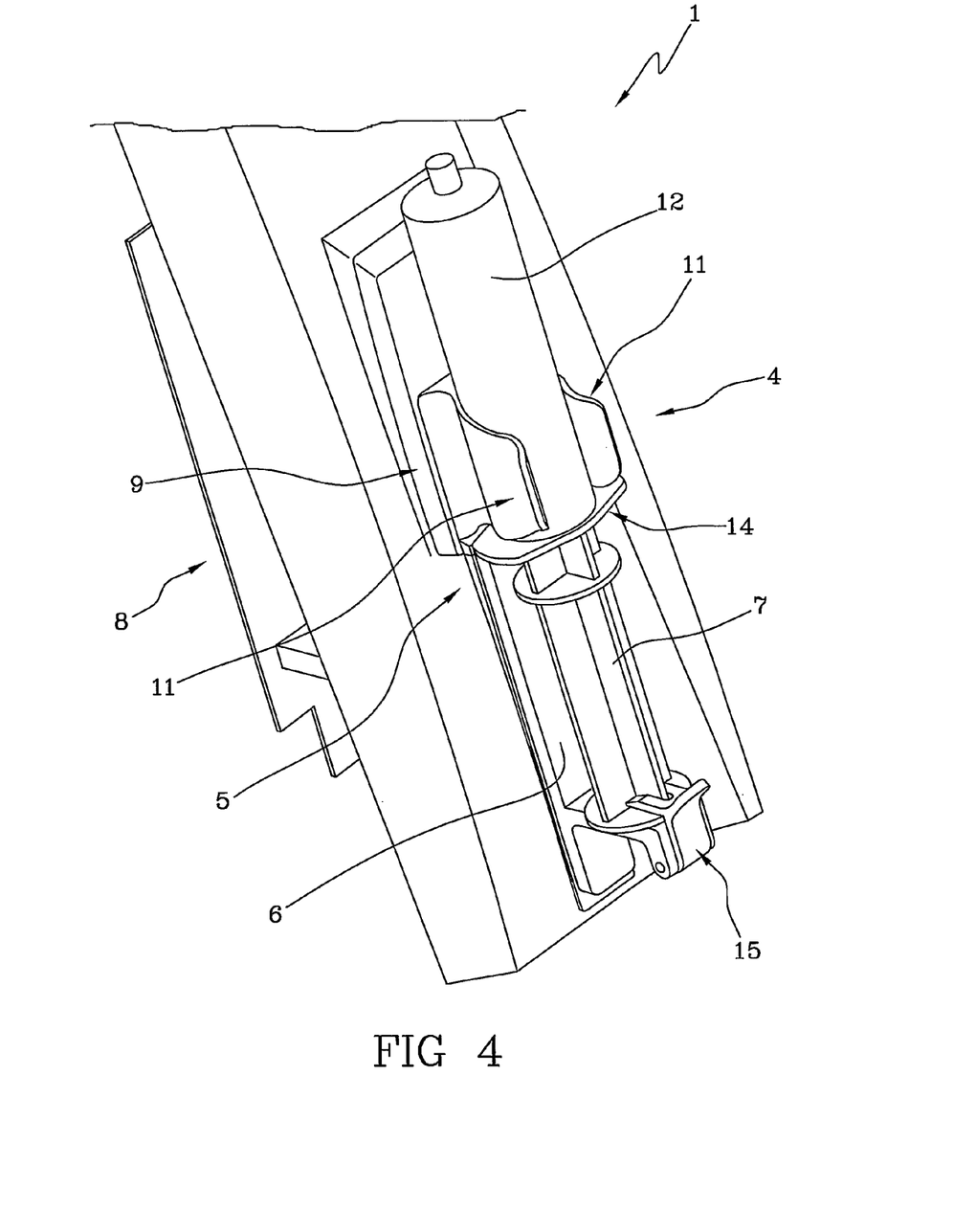
FIG. 4 is a perspective view of the support of FIG. 2, with an anticoagulant syringe mounted on the support.
Figure 5:
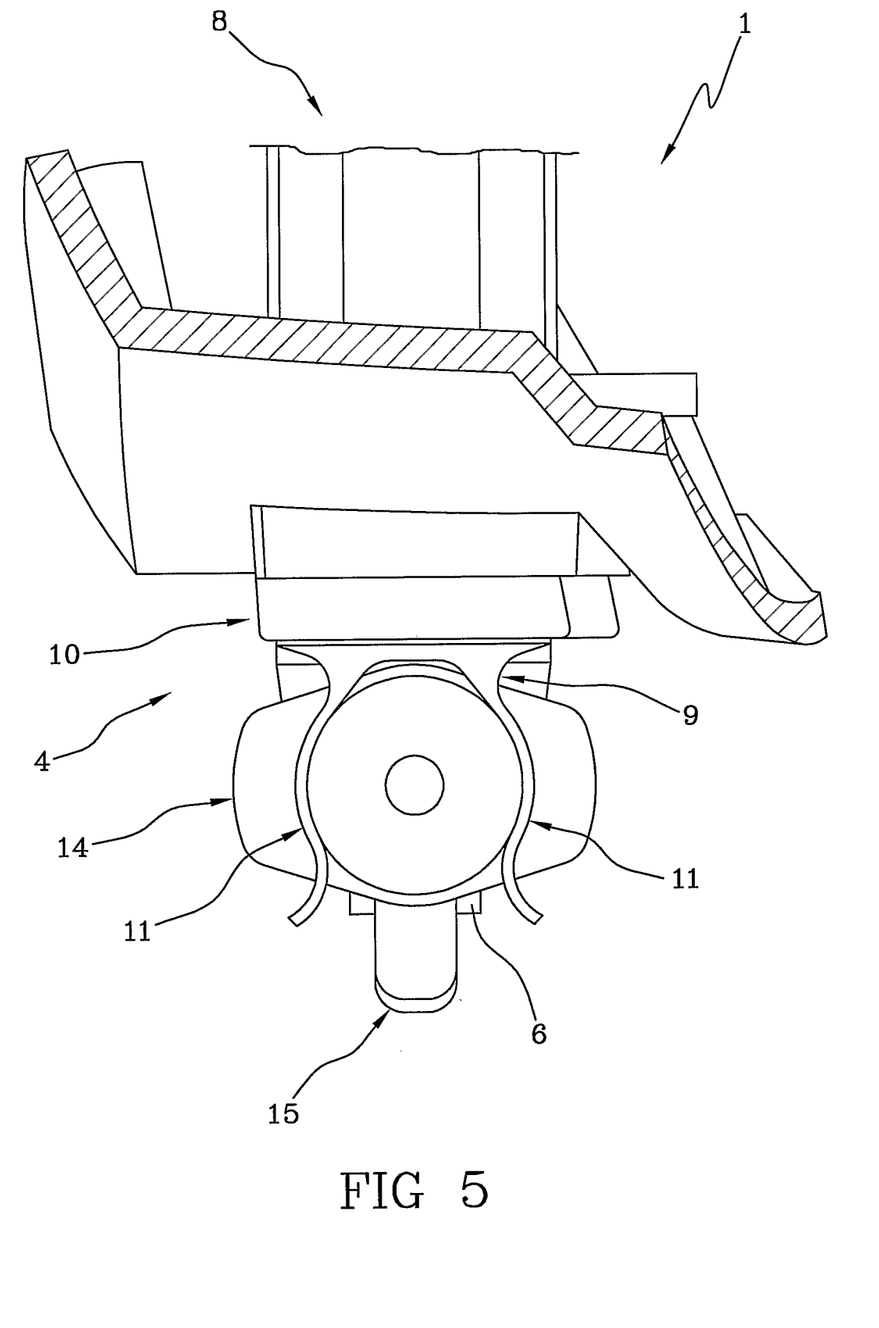
FIG. 5 is a view from above of FIG. 4.
Figure 6:
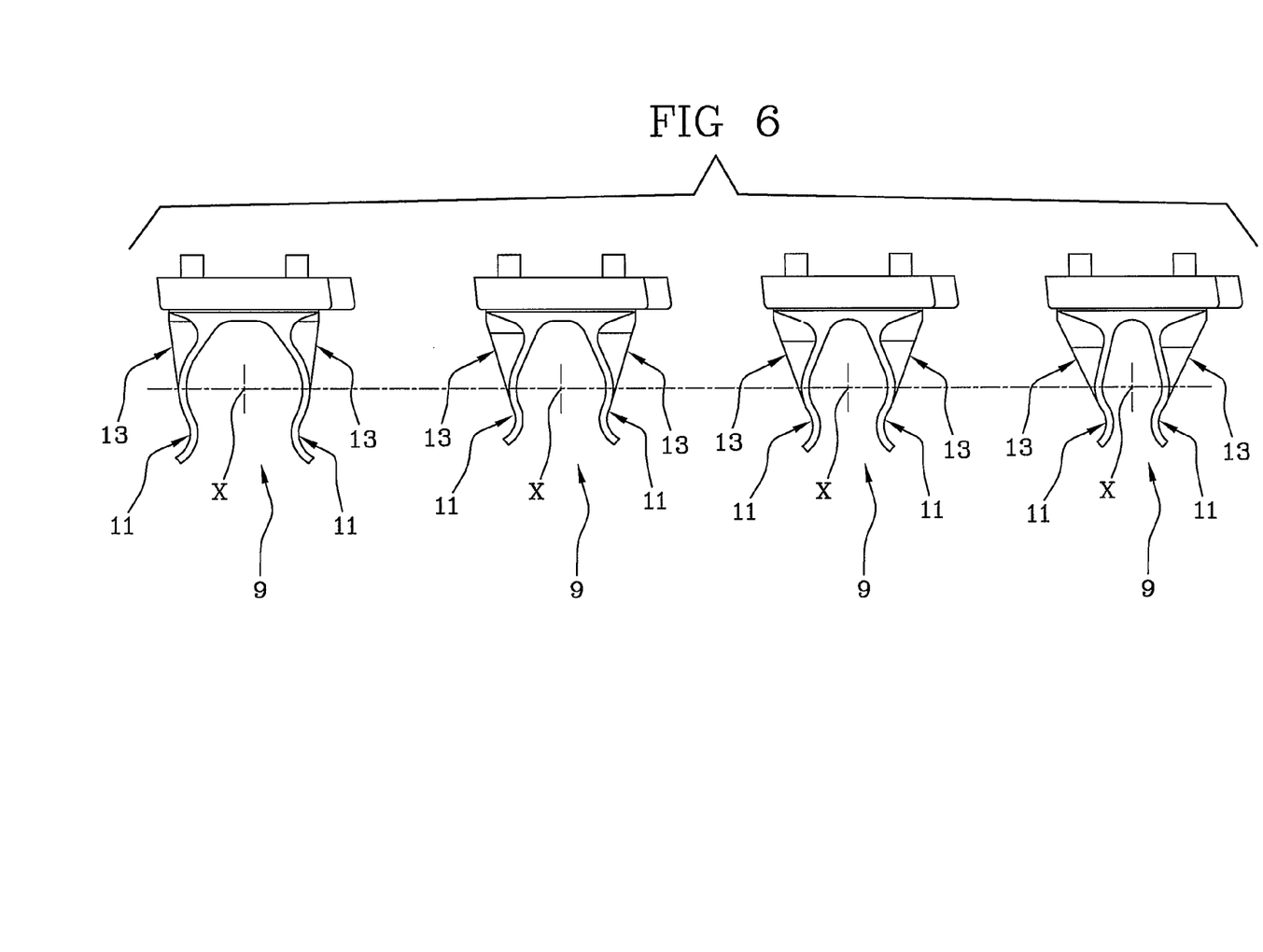
FIG. 6 includes four views from above of four different gripping elements from a set of elements according to the invention.
Figure 7:
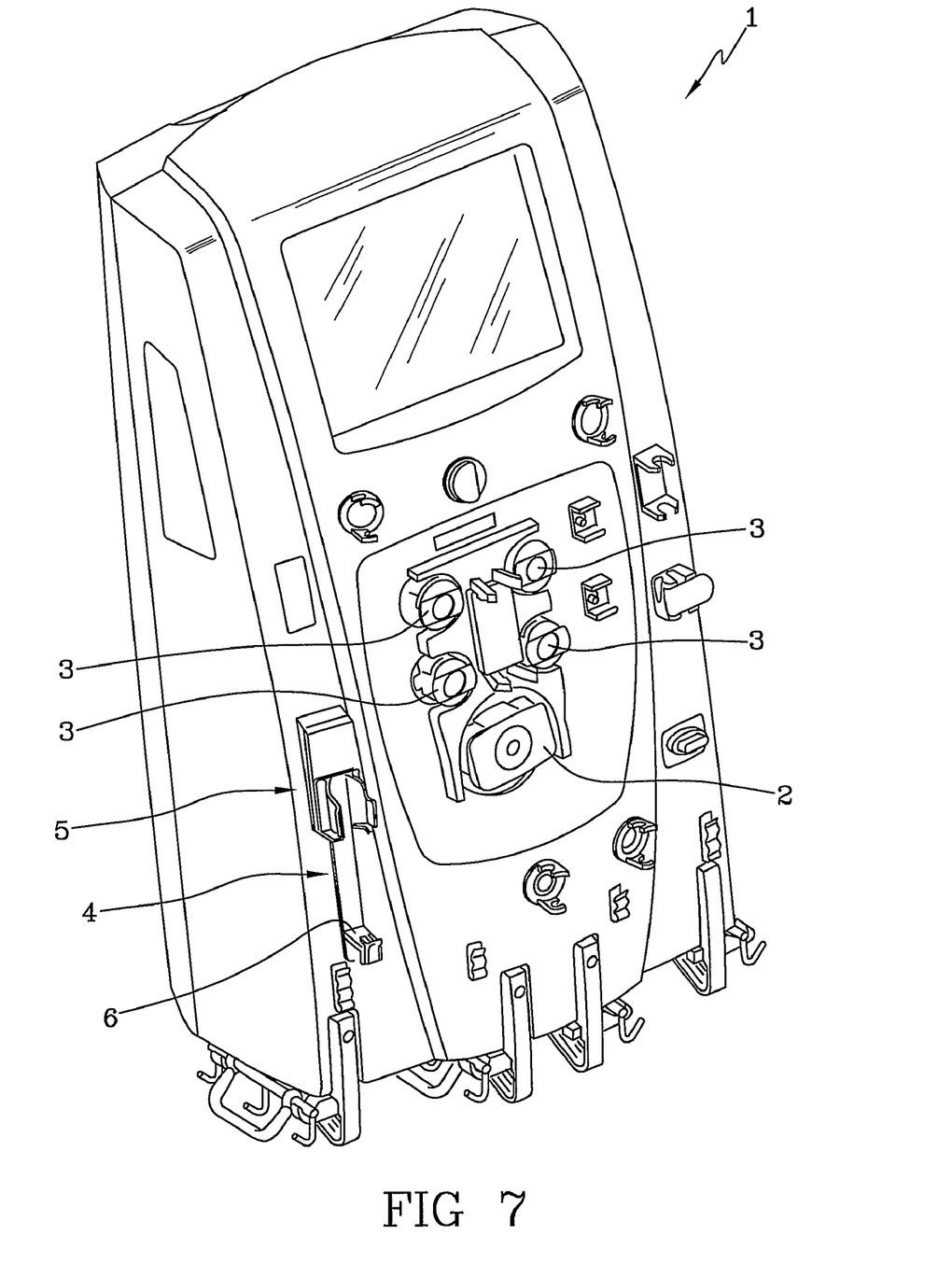
FIG. 7 is a perspective view of the dialysis machine of FIG. 1.

With reference to FIG. 7, 1 denotes in its entirety a machine for extracorporeal blood treatment, which can be used in particular for treatment of renal insufficiency, and/or for therapeutic replacement of plasma, and/or for hemoperfusion. The machine 1 comprises a blood pump 2 for blood circulation in an extracorporeal circuit. The extracorporeal circuit, of known type and not illustrated, comprises an arterial line which removes blood from a vascular access of a patient and takes it to a blood treatment unit (for example a dialysis filter), and a venous line which returns the blood to the patient after it has been treated and is outflowing from the treatment unit. The machine 1 further comprises other pumps, in the illustrated case four pumps 3, for the circulation of various liquids used in treatment, such as for example a fresh treatment liquid which is supplied to an inlet of the blood treatment unit, a used liquid discharged from an outlet of the blood treatment unit, one or more infusion liquids which are infused into the extracorporeal blood circuit. The machine 1 comprises other known-type elements, in particular various actuators and sensors (pressure sensors, blood leakage sensor, air bubble sensor, venous check valve, etc.) which are not described herein in detail. The machine 1 to which reference is made in this description is a machine for intensive extracorporeal blood treatment, sold under the name of Prismaflex®.

The machine 1 comprises a syringe pump 4 for infusion of a liquid into the extracorporeal blood circuit. In particular the syringe pump 4 is used for infusion of an anticoagulant, for example heparin, or another infusion liquid, for example a calcium solution that can be used together with a separate infusion of a citrate-based anticoagulant.

The syringe pump 4, which is described in greater detail in figures from 1 to 6, comprises a support 5 for receiving and removably holding a syringe, a linear pusher 6 for moving a mobile part 7 (plunger) of the syringe, a sensor for emitting a signal indicating the push force exerted by the plunger 6, and a control unit 8 for receiving the force signal and for guiding the linear pusher 6 according to the signal received. The force sensor is an element of known type and not described in detail: it can comprise an analog force transducer (for example a load cell). The syringe pump can be further provided with a front end-run transducer (upper) and a back end-run sensor (lower), of known type and not illustrated. A syringe pump having the characteristics as described is already used in the Prismaflex® machine, at present available commercially. The syringe pump described herein has a vertical-axis operating configuration and the following description makes reference to this configuration; however the invention is applicable to syringe pumps in which the operating position of the syringe can be of any type.

In the present invention the support 5 of the syringe pump comprises a series of interchangeable gripping elements 9 and a base, fixed to the machine frame, having a seating 10 for receiving the gripping elements 9 in a predetermined position.

The seating 10 for receiving the gripping elements 9 comprises a linear sliding guide which is parallel to the longitudinal axis of the housing of the fixed part of the syringe. In the example the sliding guide comprises a pair of parallel sliding guides, for example of the dovetail type.

Each gripping element 9 can be mounted on the seating 10 by sliding on the linear guide up to reaching an endrun position, at a predetermined operating position in which the gripping element 9 is fixed to the seating 10 using removable blocking means (for example a fastening of the screw type inserted internally of an eye in the gripping element 9).

Each gripping element 9 comprises two gripping arms 11, arranged one by the side of another, which are elastically deformable in order to embrace the diameter of a fixed part 12 (cylinder) of the syringe. A frontal opening is afforded between the two arms 11 for introducing the diameter of the fixed part of the syringe. The arms 11 are further elastically extendable in order to be able to introduce the syringe by force and to hold the syringe in position. The two arms 11 each exhibit a fixed end part 11a, rigidly constrained to a plate-shaped base body, and a curved intermediate part 11b which defines, together with the curved intermediate part 11b of the other arm, a contact surface with the fixed part 12 of the syringe. The contact surface is counter-shaped with respect to the external surface of the fixed part 12 of the syringe and is, in the illustrated example, cylindrical in shape. Each arm 11 further exhibits a free end part 11c which, together with the free end part 11c of the other arm, delimits the frontal opening for introduction of the syringe. The free end part 11c exhibits a curvature towards the outside of the frontal opening so as to define, together with the curvature of the other arm, an entry zone for facilitated introduction of the syringe diameter.

Each gripping element 9 of the series of elements 9 is conformed such as to define a housing for the fixed part 12 (cylinder) of the syringe. The housing defined by each gripping element 9 of the series has a different diameter with respect to another gripping element in the same series and also has a longitudinal axis X which coincides with a longitudinal axis of the fixed part 12 of the syringe. The difference in the housings is evident from FIG. 6, in which four different gripping elements 9 of a same series are shown: in each gripping element of a series a first portion, which is predisposed to couple with the seating fixed to the machine, is identical for all (in the preferred embodiment it comprises the plate-shaped base body), while a second portion, predisposed for removable coupling with the syringe, is different for the various elements, defining housings of various conformation but all having a longitudinal axis X (perpendicular to the sheet in FIG. 6) having a same relative position with respect to the first portion and thus with respect to the fixed seating and the pusher 6. Each gripping element 9 of the series is thus conformed and arranged in such a way that, when it is received in the seating in the predetermined operating position, the longitudinal axis X of the syringe housing is in a predetermined position with respect to the linear pusher 6. The predetermined relative position is the same for all the interchangeable gripping elements 9 in the series.

The first portion of each gripping element 9 has a counter-guide for sliding coupling with the linear guide of the fixed seating 10 of the support. The counter-guide comprises, in particular, two dove-tailed elements which are parallel for sliding coupling with the corresponding guide elements.

The gripping arms 9 exhibit an predetermined axial length so that they do not obstruct the zone of the syringe which is full of liquid, or, in other words, the zone of the syringe which is interested by the run of the mobile element (plunger) of the syringe directly operating on the liquid. The mobile part 7 of the syringe has a mobile element (plunger) which operates directly on the liquid. The mobile element exhibits a front surface which is in direct contact with the liquid to be infused. Even when the syringe is full of liquid, the front surface is situated at a certain distance from the end of the fixed part 12 of the syringe bearing the radial projection 14. The fixed part 12 (cylinder) of the syringe exhibits an axially-extended tract which is not involved with the liquid and which is comprised between the radial projection 14 and the front surface in the configuration in which the syringe if completely full. The gripping arms 11 are conformed and arranged in such a way as to embrace and hold the axial tract of the syringe i.e. the axial tract which is not involved in the run of the plunger acting directly on the liquid. Thanks to this the pushing force generating the infusion liquid flow rate (anticoagulant) is not significantly influenced by any obstruction caused by the gripping force of the support element holding the syringe tight.

Each gripping element 9 further comprises a first striker element 13 for limiting the axial movement of the fixed part of the syringe in a first direction thereof (in the illustrated embodiment in a downwards direction). The first striker element 13, which in the preferred embodiment comprises a pair of forwards-projecting fins, side by side and defining a striker plane, is positioned at a predetermined axial distance from the gripping arms 11 in order to define, together with the deformable gripping arms, a cavity for receiving a radial projection 14 of the fixed part 12 of the syringe. The radial projection comprises a ribbing normally present in known-type syringes. The deformable gripping arms 11 inferiorly define a second striker element for the radial projection, for limiting the axial movement of the fixed part of the syringe in a second direction (in the illustrated embodiment in an upwards direction) opposite the first. The deformable gripping arms 11 in effect collaborate with the first striker element 13 to hold the fixed part 12 of the syringe in position with reference to axial displacements, i.e. parallel to the longitudinal axis of the syringe pump. The gripping arms 11 collaborate with each other to immobilize the fixed part 12 of the syringe with reference to transversal displacements.

The machine 1 further comprises a sensor, not illustrated, for recognising a means for identification, also not illustrated, borne by each interchangeable gripping element 9, for sending a recognition signal of the gripping element 9 to the control unit 8. The identification device comprising the sensor and the means for identifying can be any identifying device of known type (for example mechanical and/or electronic) for recognising an interchangeable element: the identification device can comprise, for example, a sensor detecting the presence or position of a reference element, an optical sensor of a code, a sensor of an electromagnetic signal, and so on.

The linear pusher 6 is powered by a step motor, of known type and not illustrated. The pusher 6 is provided with a gripping element 15 for removably anchoring the mobile part 7 of the pump to the pusher 6. The gripping element 15 comprises a hook which is rotatable between a hooking position in which it holds in position a flanged body borne at an end of the mobile part 7 of the syringe, and a rest position (not illustrated) in which the flanged body is free.

The syringe pump, which in the described example is applied to a dialysis machine, can be applied to another type of machine for extracorporeal blood treatment, or to another type of medical apparatus (for example an infusion device).

LEGEND

1 Machine for extracorporeal blood treatment
2 Blood pump
3 Treatment liquid circulation pump
4 Syringe pump
5 Syringe support
6 Linear pusher
7 Syringe mobile part
8 Control unit
9 Interchangeable gripping elements
10 Seating for gripping elements
11 Gripping arms
11a Fixed end part
11b Intermediate part
11c Free end part
12 Syringe fixed part
13 First striker element
14 Radial projection of the syringe fixed part
15 Gripping element of the syringe mobile part
X Longitudinal axis of the syringe pump

The invention claimed is:

1. A syringe pump comprising a base, a first interchangeable gripping element, a second interchangeable gripping element, a pusher, a sensor and a control unit, the pusher being effective to move a mobile part of a syringe held in the syringe pump,
the sensor being configured to emit a force signal corresponding to a pushing force exerted by the pusher,
the control unit being configured to receive the force signal and to guide the pusher in accordance with the force signal received, the base having a linear sliding guide, the first gripping element being engaged with the base via sliding engagement with the linear sliding guide, the first gripping element comprising a first housing defining a first diameter and a first longitudinal axis, the first longitudinal axis being in a first predetermined position relative to the pusher, the first gripping element, via the first housing, being effective to hold an axial tract of a fixed part of a first syringe in a first operating position, the first syringe in the first operating position having a longitudinal axis which substantially coincides with the first longitudinal axis, the second gripping element, when the first gripping element is removed from the base, being engageable with the base via sliding engagement with the linear sliding guide, the second gripping element comprising a second housing defining a second diameter and a second longitudinal axis, the second diameter being larger than the first diameter, the second gripping element, via the second housing, being effective to hold an axial tract of a fixed part of a second syringe in a second operating position wherein the second syringe in the second operating position has a longitudinal axis which substantially coincides with the second longitudinal axis, the second longitudinal axis, when the second gripping element is engaged with the base, being in a second predetermined position relative to the pusher, the second predetermined position being the same as the first predetermined position, the linear sliding guide extending substantially parallel to the first longitudinal axis.

2. The pump of claim 1, comprising a sensor for detecting a means for identification borne by each interchangeable gripping element and for sending a recognition signal of the gripping element to the control unit.

3. The pump of claim 1, wherein the linear sliding guide comprises a pair of parallel sliding guides.

4. The pump of claim 3, wherein the pair of parallel sliding guides comprises guides of a dovetail type.

5. The pump of claim 1, wherein the axial tract of the first syringe is not involved in a run of a mobile element of the first syringe acting on a liquid contained in the first syringe.

6. The syringe pump of claim 1, wherein each of the first and second housings comprises a pair of gripping arms, each pair of gripping arms providing a frontal opening between the two gripping arms for introducing a diameter of a fixed part of a syringe, each of said gripping arms being elastically deformable so that the fixed part of the first syringe may be forced between the gripping arms of the first housing and the fixed part of the second syringe may be forced between the gripping arms of the second housing.

7. The syringe pump of claim 6, each gripping element further comprising a striker element for limiting axial movement in a first direction of a fixed part of a syringe, each striker element being positioned at an axial position from its respective gripping arms effective to define, in collaboration with the gripping arms, a cavity for receiving a radial projection of a fixed part of a syringe, the respective gripping arms defining a second striker element for the radial projection for limiting axial movement of the fixed part of the syringe in a second direction which is opposite the first direction.

8. The syringe pump of claim 6, wherein the gripping arms of the first housing are adapted to embrace less than the entire length of the fixed part of the first syringe and the gripping arms of the second housing are adapted to embrace less than the entire length of the fixed part of the second syringe.

9. The syringe pump of claim 1, wherein the base is mounted on a machine for extracorporeal blood treatment.

10. The syringe pump of claim 1, further comprising a third interchangeable gripping element, the third gripping element, when the first gripping element is removed from the base, being engageable with the base via sliding engagement with the linear sliding guide, the third gripping element comprising a third housing defining a third diameter and a third longitudinal axis, the third diameter being larger than the second diameter, the third gripping element, via the third housing, being effective to hold an axial tract of a fixed part of a third syringe in a third operating position wherein the third syringe in the third operating position has a longitudinal axis which substantially coincides with the third longitudinal axis, the third longitudinal axis, when the third gripping element is engaged with the base, being in a third predetermined position relative to the pusher, the third predetermined position being the same as the first predetermined position.

11. A machine for extracorporeal blood treatment, comprising:
a blood pump for blood circulation in an extracorporeal circuit; and
a syringe pump for infusion of a liquid in the extracorporeal blood circuit;
wherein the syringe pump is according to claim 1.

* * * * *

UNITED STATES PATENT AND TRADEMARK OFFICE
CERTIFICATE OF CORRECTION

PATENT NO. : 8,403,874 B2  
APPLICATION NO. : 11/996730  
DATED : March 26, 2013  
INVENTOR(S) : Vincenzo Baraldi Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 657 days.

Signed and Sealed this

First Day of September, 2015

Michelle K. Lee
*Director of the United States Patent and Trademark Office*